United States Patent
Alvarez

(10) Patent No.: US 11,821,588 B2
(45) Date of Patent: *Nov. 21, 2023

(54) SYSTEMS AND METHODS FOR ANALYZING MULTIPHASE PRODUCTION FLUIDS UTILIZING A VERTICALLY ORIENTED FLUIDIC SEPARATION CHAMBER COMPRISING AN OPTICALLY TRANSPARENT PIPE

(71) Applicant: Saudi Arabian Oil Company, Dhahran (SA)

(72) Inventor: Jose Oliverio Alvarez, Houston, TX (US)

(73) Assignee: Saudi Arabian Oil Company, Dhahran (SA)

(*) Notice: Subject to any disclaimer, the term of this patent is extended or adjusted under 35 U.S.C. 154(b) by 143 days.

This patent is subject to a terminal disclaimer.

(21) Appl. No.: 17/462,816

(22) Filed: Aug. 31, 2021

(65) Prior Publication Data

US 2022/0065403 A1  Mar. 3, 2022

Related U.S. Application Data

(60) Provisional application No. 63/072,358, filed on Aug. 31, 2020.

(51) Int. Cl.
*F17D 3/18* (2006.01)
*G01N 33/28* (2006.01)
(Continued)

(52) U.S. Cl.
CPC .............. *F17D 3/18* (2013.01); *F17D 3/05* (2013.01); *F17D 5/00* (2013.01); *G01N 33/2841* (2013.01)

(58) Field of Classification Search
CPC .... F17D 3/18; F17D 3/05; F17D 5/00; G01N 33/2841; G01F 1/74; G01F 15/08; E21B 43/34
See application file for complete search history.

(56) References Cited

U.S. PATENT DOCUMENTS 4,881,412 A   11/1989   Northedge
6,257,070 B1 *  7/2001  Giallorenzo ............ G01F 15/08
                                            73/861.04
(Continued)

FOREIGN PATENT DOCUMENTS

DE    600107742 T2    5/2005
GB    2213405 A       8/1989
(Continued)

OTHER PUBLICATIONS

Dr. Semih Eser, Natural Gas Composition and Specifications 2018 Penn State, Wayback Machine 2018 (Year: 2018).*
(Continued)

*Primary Examiner* — Eric S. McCall
*Assistant Examiner* — Timothy P Graves
(74) *Attorney, Agent, or Firm* — DINSMORE & SHOHL LLP

(57) ABSTRACT

System and methods for analyzing a multiphase production fluid, calculating production fluid phase flow rates, and calculating an oil/gas and oil/gas/water volume fractions of the multiphase production fluid, are provided. Contemplated systems and method may utilize fluidic piping, a production fluid supply valve, a fluidic separation chamber, an inert gas exhaust valve, a separation chamber pressure sensor, a fluidic separation detector, and a fluidic supply and analysis unit.

28 Claims, 1 Drawing Sheet

(51) Int. Cl.
  *F17D 3/05*     (2006.01)
  *F17D 5/00*     (2006.01)

(56) References Cited

U.S. PATENT DOCUMENTS

| | | |
|---|---|---|
| 9,114,332 B1 | 8/2015 | Liu et al. |
| 2005/0011646 A1* | 1/2005 | Appleford .......... B01D 21/0024 |
| | | 166/267 |
| 2005/0033684 A1 | 2/2005 | Benedyk et al. |
| 2009/0301189 A1* | 12/2009 | Ross, Jr. .............. G01F 23/268 |
| | | 73/304 C |

FOREIGN PATENT DOCUMENTS

| | | |
|---|---|---|
| WO | 2004065913 A2 | 8/2004 |
| WO | 201143084 A1 | 11/2011 |

OTHER PUBLICATIONS

Search Report pertaining to Application No. PCT/US2021/048455 dated Nov. 24, 2021.
Search Report pertaining to Application No. PCT/US2021/048446 dated Nov. 18, 2021.

* cited by examiner

SYSTEMS AND METHODS FOR ANALYZING MULTIPHASE PRODUCTION FLUIDS UTILIZING A VERTICALLY ORIENTED FLUIDIC SEPARATION CHAMBER COMPRISING AN OPTICALLY TRANSPARENT PIPE

CROSS-REFERENCE TO RELATED APPLICATIONS

This application claims the benefit of U.S. Provisional Application Ser. No. 63/072,358, filed Aug. 31, 2020 (SA 6566 MA).

BACKGROUND

The present disclosure relates to the analysis of multiphase production fluids and, more particularly, to the analysis of multiphase flow in the oil and gas industries, where multiphase flow often involves the simultaneous flow of oil, water and gas.

BRIEF SUMMARY

Multiphase flow occurs in almost all producing oil and gas wells and surface pipes that transport produced fluids. The present disclosure introduces a novel way to obtain fluid volume fractions and gas/liquid flow rates in a multiphase production fluid. The system does not require calibration and can give results that are very close to ground truth measurements. Generally, the systems and methodology of the present disclosure contemplate the use of a relatively large fluidic separation chamber that can be coupled to a surface production pipe carrying the multiphase production fluid.

Generally, in accordance with some embodiments of the present disclosure, systems for analyzing a multiphase production fluid are provided comprising fluidic piping, a production fluid supply valve, a fluidic separation chamber, an inert gas exhaust valve, a separation chamber pressure sensor, a fluidic separation detector, and a fluidic supply and analysis unit. The fluidic piping is configured to supply multiphase production fluid from the production fluid supply valve to the fluidic separation chamber. The inert gas exhaust valve is configured to exhaust inert gas from the fluidic separation chamber. The separation chamber pressure sensor is configured to provide an indication of gas pressure in the fluidic separation chamber. The fluidic supply and analysis unit is in communication with the production fluid supply valve, the inert gas exhaust valve, and the separation chamber pressure sensor, and is configured to (i) communicate with the production fluid supply valve to supply a multiphase production fluid to the fluidic separation chamber, (ii) communicate with the separation chamber pressure sensor and the inert gas exhaust valve to stabilize gas pressure within the fluidic separation chamber, (iii) communicate with the fluidic separation detector to monitor a growth rate $Q_C$ of a gaseous phase column of the multiphase production fluid in the fluidic separation chamber, and (iv) convert the growth rate $Q_C$ of the gaseous phase column to a production fluid gas flow rate $Q_G$. The aforementioned communication may be one-way or two-way communication.

The fluidic supply and analysis unit can be configured to transition the fluidic separation chamber to a static state after a complete gaseous phase column and a complete oil phase column are formed within the fluidic separation chamber. In the static state, the fluidic supply and analysis unit communicates with the fluidic separation detector to measure the absolute or relative sizes of the complete gaseous phase column and the complete oil phase column and calculates an oil/gas volume fraction as a function of the measured sizes of the gaseous phase and oil phase columns in the fluidic separation chamber. Embodiments are also contemplated where the absolute or relative sizes of the complete gaseous phase column, the complete oil phase column, and the complete water phase column are measured and used to calculate a volume fraction $V_O/V_G/V_{H2O}$ as a function of the measured sizes of the gaseous phase, oil phase, and water phase columns.

Generally, in accordance with other embodiments, the present disclosure introduces methodology for analyzing a multiphase production fluid by supplying an inert gas to a vertically-oriented fluidic separation chamber, the inert gas being lighter than a gaseous phase of the multiphase production fluid. A multiphase production fluid is supplied to the fluidic separation chamber through a production fluid supply valve and the pressure of the inert gas in the fluidic separation chamber, as sensed by a separation chamber pressure sensor, is stabilized utilizing an inert gas exhaust valve. A fluidic separation detector and a fluidic supply and analysis unit are utilized to monitor a growth rate $Q_C$ of a gaseous phase column of the multiphase production fluid in the fluidic separation chamber, and convert the growth rate $Q_C$ of the gaseous phase column to a production fluid gas flow rate $Q_G$.

According to further embodiments, the fluidic supply and analysis unit transitions the fluidic separation chamber to a static state after a complete gaseous phase column and a complete oil phase column are formed within the fluidic separation chamber. As these complete phases are formed, the fluidic supply and analysis unit communicates with the fluidic separation detector to measure the absolute or relative sizes of the complete gaseous phase column and the complete oil phase column, and calculates an oil/gas volume fraction as a function of the measured sizes of the gaseous phase and oil phase columns in the fluidic separation chamber.

In further embodiments, the fluidic separation chamber is not transitioned to the static state until after a complete gaseous phase column, a complete oil phase column, and a complete water phase column are formed within the fluidic separation chamber. This allows the fluidic supply and analysis unit to measure the absolute or relative sizes of the complete gaseous phase column, the complete oil phase column, and the complete water phase columns, and calculate a volume fraction $V_O/V_G/V_{H2O}$ as a function of the measured sizes of the gaseous phase, oil phase, and water phase columns.

BRIEF DESCRIPTION OF THE SEVERAL VIEWS OF THE DRAWING

The following detailed description of specific embodiments of the present disclosure can be best understood when read in conjunction with the following drawing, where like structure is indicated with like reference numerals and in which.

DETAILED DESCRIPTION

Figure 1:
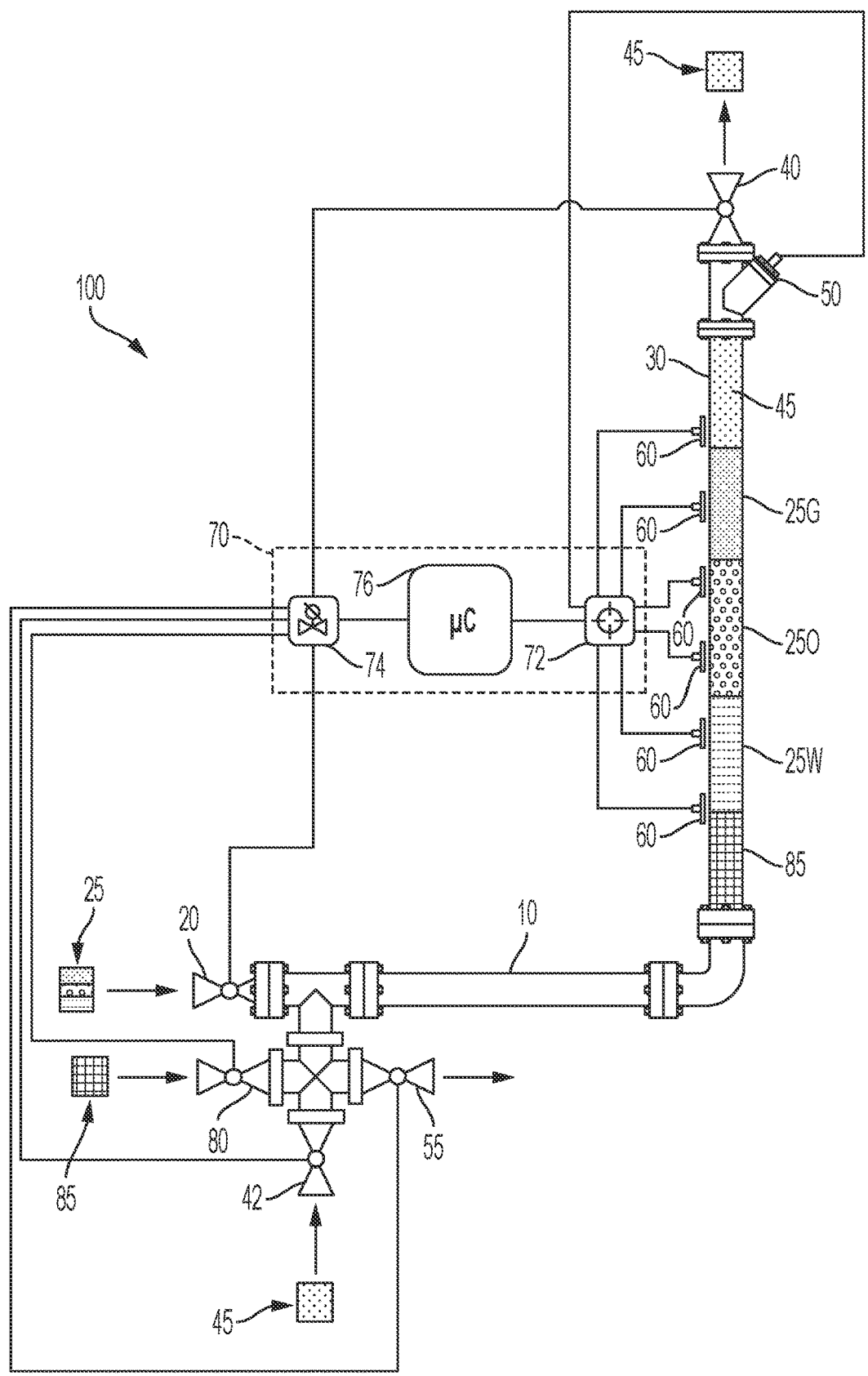
FIG. 1 illustrates systems and methodology for analyzing a multiphase production fluid according to the present disclosure.

Referring to FIG. 1, a system 100 for analyzing a multiphase production fluid according to the present disclosure may comprise fluidic piping 10, a production fluid supply valve 20 a fluidic separation chamber 30, an inert gas exhaust valve 40, a separation chamber pressure sensor 50, a fluidic separation detector 60, and a fluidic supply and analysis unit 70. The production fluid supply valve 20 can be used to divert multiphase production fluid 25 from a surface production conduit of, for example, an oil or gas production operation.

The fluidic piping 10 is configured to supply multiphase production fluid 25 from the production fluid supply valve 20 to the fluidic separation chamber 30. The inert gas exhaust valve 40 is configured to exhaust inert gas 45 from the fluidic separation chamber 30. The inert gas 45, which may be supplied via an inert gas supply valve 42, has a lower density than the gaseous phase of the multiphase production fluid. For example, the inert gas may comprise helium, neon, or combinations thereof.

The fluidic supply and analysis unit 70 is in communication with the production fluid supply valve 20, the inert gas exhaust valve 40, the separation chamber pressure sensor 50, and potentially, other components of the system 100, as will be described in further detail below. The fluidic supply and analysis unit 70 communicates with the production fluid supply valve 20 to supply multiphase production fluid 25 to the fluidic separation chamber 30. The fluidic supply and analysis unit 70 also communicates with the separation chamber pressure sensor 50, which is configured to provide an indication of gas pressure in the fluidic separation chamber 30, and the inert gas exhaust valve 40, to stabilize gas pressure within the fluidic separation chamber 30. Additionally, the fluidic supply and analysis unit 70 communicates with the fluidic separation detector 60 to monitor a growth rate $Q_C$ of a gaseous phase column 25G of the multiphase production fluid 25 in the fluidic separation chamber 30, and convert the growth rate $Q_C$ of the gaseous phase column 25G to a production fluid gas flow rate $Q_G$.

In one embodiment of the present disclosure, the growth rate $Q_C$ of the gaseous phase column 25G is converted to the production fluid gas flow rate $Q_G$ by accounting for a gravitational separation rate $Q_S$ of the gaseous phase column 25G resulting from gravitational forces in the fluidic separation chamber 30. This gravitational separation can be optimized by ensuring that the fluidic separation chamber 30 is vertically oriented, and can be represented as $Q_G=Q_C-Q_S$.

Although the growth rate $Q_C$ of the gaseous phase column 25G can be converted to the production fluid gas flow rate $Q_G$ in a variety of ways, in one embodiment, it is converted by (i) measuring a change of height $\Delta h$ of the gaseous phase column 25G over a time $\Delta t$, (ii) calculating an increase in gaseous volume $\Delta V$ as a function of $\Delta h$ and a cross sectional area of fluidic separation chamber 30, and (iii) calculating the production fluid gas flow rate $Q_G$ as a function of $\Delta V$ and a gravitational separation rate $Q_S$. The gravitational separation rate $Q_S$ can be a predetermined value that is obtained from a sample of the multiphase production fluid and helps account for volumetric growth of the gaseous phase column 25G resulting from gravitational forces in the fluidic separation chamber 30. To ensure the accuracy of this conversion, it can be helpful to ensure that a complete gaseous phase column 25G resides within the fluidic separation chamber 30 over the time $\Delta t$. In other words, a sufficient volume of multiphase production fluid 25 should be introduced into the system 100, via the production fluid supply valve 20, to ensure that a complete gaseous phase column 25G resides within the fluidic separation chamber 30 over the time $\Delta t$.

In some embodiments, it may be preferable to include a baseline liquid supply valve 80 in the system 100. In such embodiments, a heavy water, or heavier-than-water, baseline liquid 85 can be used to move a fixed volume of the multiphase production fluid 25 into the fluidic separation chamber 30, as is illustrated in FIG. 1. More specifically, the supply and analysis unit 70 can be configured to supply sufficient volumes of the multiphase production fluid 25 and the baseline liquid 85 to the fluidic separation chamber 30 via the production fluid supply valve 20 and the baseline liquid supply valve 80 to ensure that a complete gaseous phase column 25G resides within the fluidic separation chamber 30 over the time $\Delta t$.

The present inventors have recognized distinct diagnostic improvements if laminar flow in the multiphase production fluid 25 is preserved in the fluidic piping 10. For example, with laminar flow, it is contemplated that gravitational separation in the fluidic separation chamber 30 will be enhanced, and may occur more rapidly, if laminar flow is maintained. This also helps keep the required height of the fluidic separation chamber 30 from becoming too large because particular diagnostic modes of the present disclosure require extended active flow regimes where a specific degree of separation is required. To this end, it may be preferable to configure the fluidic supply and analysis unit 70 to maintain a preferred pressure drop across the multiphase production fluid flow in the fluidic piping 10 and the fluidic separation chamber 30. This pressure drop can be measured with the aid of the separation chamber pressure sensor 50. Although a wide range of suitable pressure drops are contemplated by the present disclosure, e.g., up to about 1000 kPa, in practice, the pressure drop will depend on the length of the fluidic separation chamber 30, particularly where it is vertically oriented. For example, and not by way of limitation, with a fluidic separation chamber 30 having a length in the range of 30 m to 100 m, suitable pressure drops may be between 500 kPa and 1000 kPa, as this would be more likely to maintain the average velocity of the multiphase production fluid low enough to keep the flow laminar (Re<3000). If, for logistical reasons, the length of the fluidic separation chamber is shorter, e.g., about 10 meters in height, then a smaller pressure drop would be required to reduce the velocity even more and give time for the phases to have measurable separation in the fluidic separation chamber. For example, a 10 meter fluidic separation chamber may require a pressure drop of less than 10 kPa. Longer fluidic separation chambers, e.g., about 50 meters in height may require pressure drops of about 700 KPa.

The aforementioned pressure drop can be maintained by controlling the inert gas exhaust valve 40, the production fluid supply valve 20, or both. Depending on the fluid content, the average velocity of the multiphase fluid in the fluid analysis system 100 is maintained so that it is less than about 0.5 m/s. In some embodiments, it will be sufficient to ensure that the fluidic supply and analysis unit 70 is configured to keep multiphase production fluid flow in the fluidic piping 10 and the fluidic separation chamber 30 slow enough to ensure that at least 50% of the volumetric growth of the gaseous phase column 25G in the fluidic separation chamber 30 is a result of gravitational forces.

To help stabilize the pressure drop, the separation chamber pressure sensor 50 can be positioned in the fluidic separation chamber 30 to sense gas pressure of the inert gas 45 in the fluidic separation chamber 30. The fluidic supply and analysis unit 70 is placed in communication with the pressure sensor 50 and can be configured to stabilize gas pressure within the fluidic separation chamber 30 by controlling the inert gas exhaust valve 40. Pressure can also be stabilized by controlling the rate at which multiphase production fluid 25 is supplied via the production fluid supply valve 20. In any case, it is contemplated that the pressure can be stabilized by holding the gas pressure constant, or by controlling the pressure in some other diagnostically recognizable way, to enable analysis. In other words, a "stabilized" pressure need not be a constant pressure.

In embodiments where a baseline liquid 85 is available for introduction via the baseline liquid supply valve 80, the fluidic supply and analysis unit 70 can be configured to stabilize gas pressure within the fluidic separation chamber by further controlling a rate at which the baseline liquid 85 is supplied to the fluidic piping 10 via the baseline liquid supply valve 80. Depending on the particular control scheme used to control gas pressure within the fluidic separation chamber 30, the various valves described herein, i.e., the production fluid supply valve 20, the inert gas exhaust valve 40, and the baseline liquid supply valve 80, may be continuously variable valves defining a wide range of admissible flow rates, or more simple valves that merely transition between "on" and "off" states.

The fluidic supply and analysis unit 70 can be configured to provide volume fraction data by transitioning the fluidic separation chamber 30 to a static state after a complete gaseous phase column 25G and a complete oil phase column 25O are formed within the fluidic separation chamber 30. Once formed, the fluidic supply and analysis unit 70 communicates with the fluidic separation detector 60 to measure the absolute or relative sizes of the complete gaseous phase column 25G and the complete oil phase column 25O. Oil/gas volume fractions can be calculated as a function of the measured sizes of the gaseous phase and oil phase columns 25G, 25O in the fluidic separation chamber 30.

In some cases, the complete oil phase column 25O may comprise an oil/water emulsion, particularly if the properties of the multiphase production fluid are such that complete separation of the oil and water phases by gravity is not practical. In such cases, it may be advantageous to configure the fluidic supply and analysis unit 70 to calculate the oil/gas volume fraction as a function of an emulsification factor that can be used to estimate the respective volumetric proportions of the oil and water phases of the oil/water emulsion forming the complete oil phase column 25O. This emulsification factor can be obtained experimentally using demulsifiers.

Those practicing the concepts of the present disclosure will appreciate that a number of different factors can be used to determine if the gas and oil columns 25G, 25O are "complete." For example, in some embodiments, the fluidic supply and analysis unit 70 will calculate the oil/gas volume fraction after a growth rate of the gaseous phase column 25G, the oil phase column 25O, or both, drops below a growth rate threshold. In other embodiments, the oil/gas volume fraction will be calculated after a threshold separation time has elapsed, or after the oil phase column 25O and the gaseous phase column 25G have reached between about 50% and about 80% of their fully separated sizes. More specifically, although it may be advantageous to ensure substantially complete separation of the oil and gas phases of the production fluid 25 in the fluidic separation chamber 30, because of time constraints, in many embodiments, where the volume of a water/oil emulsion is not expected to be considerable, it may be sufficient to ensure that the oil phase column 25O and the gaseous phase column 25G have merely reached a degree of separation that is diagnostically significant.

It is also noted that the calculated oil/gas volume fractions according to the present disclosure may represent absolute or proportional volumes of oil and gas in the fluidic separation chamber 30. More specifically, embodiments are contemplated where the oil/gas volume fraction represents respective oil and gas volumes relative to each other, or relative to a total volume of the multiphase production fluid in the fluidic separation chamber.

Given a calculated volume fraction, the fluidic supply and analysis unit 70 can be configured to calculate a production fluid oil flow rate $Q_O$ as a function of at least the production fluid gas flow rate $Q_G$ and the volume fraction $V_O/V_G$. More specifically, as $Q_O=Q_G(V_O/V_G)$.

The fluidic supply and analysis unit 70 can be configured to transition the fluidic separation chamber 30 to a static state by stopping the supply of multiphase production fluid 25 via the production fluid supply valve 20. In embodiments where the system 100 further comprises a baseline liquid supply valve 80, and the fluidic piping 10 supplies baseline liquid 85 from the baseline liquid supply valve 80, the fluidic supply and analysis unit 70 can be configured to transition the fluidic separation chamber 30 to a static state by replacing the supply of multiphase production fluid 25 with baseline liquid 85 and subsequently stopping the supply of baseline liquid 85.

In additional embodiments, oil/gas/water volume fractions can be calculated as a function of the measured sizes of the gaseous phase, oil phase, and water phase columns 25G, 25O, 25W in the fluidic separation chamber 30. More specifically, The fluidic supply and analysis unit 70 can be configured to transition the fluidic separation chamber 30 to the aforementioned static state after a complete gaseous phase column 25G, a complete oil phase column 25O, and a complete water phase column 25W are formed within the fluidic separation chamber 30, as is illustrated in FIG. 1. Once formed, the fluidic supply and analysis unit 70 communicates with the fluidic separation detector to measure the absolute or relative sizes of the complete gaseous phase column 25G, the complete oil phase column 25O, and the complete water phase column 25W, and calculate a volume fraction $V_O/V_G/V_{H2O}$ as a function of the measured sizes of the gaseous phase, oil phase, and water phase columns 25G, 25O, 25W in the fluidic separation chamber 30. In such embodiments, the fluidic supply and analysis unit 70 can be configured to calculate a production fluid oil flow rate $Q_O$ and a production fluid water flow rate $Q_{H2O}$ as a function of at least the production fluid gas flow rate $Q_G$ and the volume fraction $V_O/V_G/V_{H2O}$. For example, in one embodiment, where a 2-3 meter column of the multiphase production fluid 25 is supplied at a rate of approximately 0.2 m/s, through supply and separation pipe of about 4 inches in diameter, given a separation time of about 2 minutes, a 30 meter fluidic separation chamber 30 will be large enough to accommodate the necessary entry and separation of the multiphase production fluid 25 in the fluidic separation chamber 30. Shorter chamber lengths will be suitable for lower flow rates, or if less time is needed to ensure sufficient separation.

As is implied above, in embodiments where a baseline liquid 85 is supplied via a baseline liquid supply valve 80, the fluidic supply and analysis unit 70 can be configured to communicate with the baseline liquid supply valve 80 to replace the supply of multiphase production fluid 25 with baseline liquid 85. In this manner, the baseline liquid 85 can be used to ensure that a complete gaseous phase column 25G, a complete oil phase column 25O, and/or a complete water phase column 25W will resides within the fluidic separation chamber 30.

As is illustrated in FIG. 1, the system 100 may further comprise a production fluid drain valve 55, and the fluidic piping 10 may be configured to drain production fluid from the fluidic separation chamber 30 through the production fluid drain valve 55. In this manner, separated fluids may be returned to the production system through the production fluid drain valve 20. Alternatively, it is contemplated that separated fluids may be returned through the baseline liquid supply valve 80.

Although the fluidic piping 10 and the fluidic separation chamber 30 are merely illustrated schematically in FIG. 1, it is contemplated that the fluidic piping 10 and the fluidic separation chamber 30 may comprise cylindrical piping of matching cross sectional dimensions. In many embodiments, it will also be preferable to ensure that the fluidic separation chamber 30 comprises an optically transparent cylindrical pipe, as this will enhance the ability of particular types of fluidic separation detectors 60, like an optical vision system defining a field of view encompassing the transparent pipe, to provide meaningful separation data. It will also be advantageous, in many embodiments, to ensure that the fluidic separation chamber 30 is vertically oriented and the system is configured such that the multiphase production fluid 25 assumes a vertical orientation in the fluidic separation chamber 30, as this will enhance gravitational phase separation.

As will be appreciated by those familiar with fluidic control systems and fluidic detection, the fluidic supply and analysis unit 70 may be presented in a variety of configurations. For example, and not by way of limitation, the fluidic supply and analysis unit 70 may comprise a fluidic separation detection module 72, a fluidic metering module 74, and a programmable controller 76. In such embodiments, the fluidic separation detection module 72 would be in communication with the fluidic separation detector 60. In addition, the fluidic metering module 74 would be in communication with the production fluid supply valve 25, the inert gas exhaust valve 40, and the separation chamber pressure sensor 50. Collectively, the fluidic separation detection module 72 and the fluidic metering module 74 would be in communication with the programmable controller 76. In these types of implementations, it is contemplated that the stated modules would comprise memory and other electronic components suited to complement the functionality of the corresponding detector(s), valve(s), and sensor(s) with which they communicate. Alternatively, the functionality of the stated modules and controller could be accommodated in a single, programmable unit or control hub.

Those practicing the present invention, and familiar with fluidic detection will appreciate that the system 100 may comprise a plurality of fluidic separation detectors 60, as is illustrated in FIG. 1, where a plurality of fluidic separation detectors 60 are arranged along a longitudinal dimension of the fluidic separation chamber 30. In addition, it is contemplated that a variety of detectors 60 will be suitable for providing useful phase movement and separation data to the fluidic supply and analysis unit 70. Contemplated detectors may be presented as passive or active sensors. For example, and not by way of limitation, a non-illuminating vision system or a temperature/gas sensor array could be used as passive sensors to observe the multiphase production fluid to facilitate the aforementioned growth rate monitoring. Active sensors include, but are not limited to, microwave or acoustic transceivers, or an illuminating vision system including one or more high speed cameras. Depending on the sensing technology utilized, these detectors 60 can be arranged along the fluidic separation chamber by positioning them outside of the chamber body, or may be embedded in the chamber body, in contact, or non-contact, with the fluid receiving space of the fluidic separation chamber 30.

For the purposes of describing and defining the present invention, it is noted that reference herein to a characteristic of the subject matter of the present disclosure being a "function of" a parameter, variable, or other characteristic is not intended to denote that the characteristic is exclusively a function of the listed parameter, variable, or characteristic. Rather, reference herein to a characteristic that is a "function" of a listed parameter, variable, etc., is intended to be open ended such that the characteristic may be a function of a single parameter, variable, etc., or a plurality of parameters, variables, etc.

It is noted that recitations herein of a component of the present disclosure being "configured" in a particular way, to embody a particular property, or to function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the terms "in which" and "wherein" as transitional phrases. For the purposes of defining the present invention, it is noted that these terms are introduced in the claims as an open-ended transitional phrase that is used to introduce a given number of claim elements and should be interpreted in like manner as the more commonly used open-ended preamble term "comprising."

What is claimed is:

1. A system for analyzing a multiphase production fluid, the system comprising
fluidic piping,
a production fluid supply valve configured to supply multiphase production fluid,
an inert gas supply valve configured to supply an inert gas, the inert gas being separate from and comprising a lower density than a gaseous phase of the multiphase production fluid,
a vertically oriented fluidic separation chamber comprising an optically transparent pipe,
an inert gas exhaust valve,
a separation chamber pressure sensor,
a fluidic separation detector comprising a vision system, and
a fluidic supply and analysis unit, in which:
the fluidic piping is configured to supply multiphase production fluid from the production fluid supply valve to the vertically oriented fluidic separation chamber;
the inert gas exhaust valve is configured to exhaust inert gas from the vertically oriented fluidic separation chamber;
the separation chamber pressure sensor is configured to provide an indication of gas pressure in the vertically oriented fluidic separation chamber; and
the fluidic supply and analysis unit is in communication with the production fluid supply valve, the inert gas supply valve, the inert gas exhaust valve, the separation chamber pressure sensor, and the fluidic separation detector, and is configured to
supply the inert gas to the vertically oriented fluidic separation chamber through the inert gas supply valve,
communicate with the production fluid supply valve to supply the multiphase production fluid to the vertically oriented fluidic separation chamber through the production fluid supply valve after supplying the inert gas,
communicate with the separation chamber pressure sensor to stabilize the gas pressure within the vertically oriented fluidic separation chamber by exhausting the inert gas through the inert gas exhaust valve as the multiphase production fluid is supplied,
communicate with the fluidic separation detector to monitor a growth rate $Q_C$ of a gaseous phase column of the multiphase production fluid in the vertically oriented fluidic separation chamber through the fluidic separation detector, and
convert the growth rate $Q_C$ of the gaseous phase column to a production fluid gas flow rate $Q_G$.

2. The system as claimed in claim 1 wherein the fluidic supply and analysis unit is configured to convert the growth rate $Q_C$ of the gaseous phase column to the production fluid gas flow rate $Q_G$ by accounting for a gravitational separation rate $Q_S$ of the gaseous phase column resulting from gravitational forces in the vertically oriented fluidic separation chamber.

3. The system as claimed in claim 2 wherein $Q_G=Q_C-Q_S$.

4. The system as claimed in claim 1 wherein the fluidic supply and analysis unit is configured to convert the growth rate of the gaseous phase column to the production fluid gas flow rate $Q_G$ by:
measuring a change of height $\Delta h$ of the gaseous phase column over a time $\Delta t$;
calculating an increase in gaseous volume $\Delta V$ as a function of $\Delta h$ and a cross sectional area of the vertically oriented fluidic separation chamber; and
calculating the production fluid gas flow rate $Q_G$ as a function of $\Delta V$ and a gravitational separation rate $Q_S$, which accounts for volumetric growth of the gaseous phase column resulting from gravitational forces in the vertically oriented fluidic separation chamber.

5. The system as claimed in claim 4 wherein the fluidic supply and analysis unit is configured to supply a sufficient volume of the multiphase production fluid via the production fluid supply valve to ensure that a completely separated gaseous phase column resides within the fluidic separation chamber over the time $\Delta t$.

6. The system as claimed in claim 4 wherein:
the system further comprises a baseline liquid supply valve configured to supply a baseline liquid comprising water; and
the fluidic supply and analysis unit is configured to supply sufficient volumes of the multiphase production fluid and the baseline liquid to the fluidic separation chamber via the production fluid supply valve and the baseline liquid supply valve, respectively, to ensure that a completely separated gaseous phase column resides within the fluidic separation chamber over the time $\Delta t$.

7. The system as claimed in claim 1 wherein the fluidic supply and analysis unit is additionally configured to maintain laminar multiphase production fluid flow in the fluidic piping by maintaining a pressure drop across the multiphase production fluid flow in the fluidic piping and the fluidic separation chamber, as measured by the separation chamber pressure sensor, the pressure drop at less than about 1000 kPa.

8. The system as claimed in claim 7 wherein the pressure drop is maintained by controlling the inert gas exhaust valve, the production fluid supply valve, or both.

9. The system as claimed in claim 8 wherein the pressure drop is further maintained by controlling the average flow velocity of the multiphase production fluid in the fluid analysis system less than about 0.5 m/s.

10. The system as claimed in claim 1 wherein the fluidic supply and analysis unit is configured to keep multiphase production fluid flow in the fluidic piping and the vertically oriented fluidic separation chamber slow enough to ensure that at least 50% of the volumetric growth of the gaseous phase column in the vertically oriented fluidic separation chamber is a result of gravitational forces.

11. The system as claimed in claim 1 wherein:
the separation chamber pressure sensor is positioned in the vertically oriented fluidic separation chamber to sense the gas pressure of the inert gas in the vertically oriented fluidic separation chamber; and
the fluidic supply and analysis unit is configured to stabilize the gas pressure within the vertically oriented fluidic separation chamber by controlling the inert gas exhaust valve to stabilize the pressure of the inert gas.

12. The system as claimed in claim 11 wherein the fluidic supply and analysis unit is configured to stabilize the gas pressure within the vertically oriented fluidic separation chamber by further controlling a rate at which the multiphase production fluid is supplied via the production fluid supply valve.

13. The system as claimed in claim 12 wherein:
the system further comprises a baseline liquid supply valve configured to supply a baseline liquid comprising water; and the fluidic supply and analysis unit is configured to stabilize the gas pressure within the vertically oriented fluidic separation chamber by further controlling a rate at which the baseline liquid is supplied to the fluidic piping via the baseline liquid supply valve.

14. The system as claimed in claim 1 wherein the fluidic supply and analysis unit is configured to stabilize the gas pressure within the vertically oriented fluidic separation chamber by holding the gas pressure constant.

15. The system as claimed in claim 1 wherein:
the system further comprises a baseline liquid supply valve configured to supply a baseline liquid comprising water;
the fluidic piping is configured to supply the baseline liquid from the baseline liquid supply valve to the fluidic separation chamber; and
the fluidic supply and analysis unit is in communication with the baseline liquid supply valve and is additionally configured to replace the supply of multiphase production fluid with the baseline liquid after the multiphase production fluid is supplied to the fluidic separation chamber.

16. The system as claimed in claim 15 wherein the fluidic supply and analysis unit is additionally configured to:
continue the supply of the baseline liquid until a completely separated gaseous phase column resides within the vertically oriented fluidic separation chamber;
continue the supply of the baseline liquid until a completely separated oil phase column resides within the vertically oriented fluidic separation chamber;
continue the supply of the baseline liquid until a completely separated water phase column resides within the vertically oriented fluidic separation chamber; or
combinations thereof.

17. The system as claimed in claim 1 wherein the fluidic piping and the vertically oriented fluidic separation chamber comprise cylindrical piping of matching cross sectional dimensions.

18. The system as claimed in claim 1 wherein the system comprises a plurality of fluidic separation detectors.

19. The system as claimed in claim 18 wherein the plurality of fluidic separation detectors are arranged along a longitudinal dimension of the vertically oriented fluidic separation chamber.

20. The system as claimed in claim 1 wherein the vision system defines a field of view that encompasses the optically transparent portion of the vertically oriented fluidic separation chamber.

21. A method for analyzing a multiphase production fluid in a system comprising a production fluid supply valve configured to supply multiphase production fluid, an inert gas supply valve configured to supply an inert gas, the inert gas being separate from and comprising a lower density than a gaseous phase of the multiphase production fluid, a vertically orientated fluidic separation chamber comprising an optically transparent pipe, fluidic piping configured to supply the multiphase production fluid and the inert gas to the vertically oriented fluidic separation chamber, an inert gas exhaust valve configured to exhaust the inert gas from the vertically oriented fluidic separation chamber, a separation chamber pressure sensor configured to provide an indication of gas pressure in the vertically oriented fluidic separation chamber, a fluidic separation detector comprising a vision system, and a fluidic supply and analysis unit in communication with the production fluid supply valve, the inert gas supply valve, the inert gas exhaust valve, the separation chamber pressure sensor, and the fluidic separation detector, the method comprising:
supplying the inert gas to the vertically oriented fluidic separation chamber,
supplying at least a portion of the multiphase production fluid to the vertically oriented fluidic separation chamber through the production fluid supply valve after supplying the inert gas,
stabilizing the gas pressure within the vertically oriented fluidic separation chamber by exhausting the inert as through the inert gas valve as the multiphase production fluid is supplied to the vertically oriented fluidic separation chamber,
monitoring a growth rate $Q_C$ of a gaseous phase column of the multiphase production fluid in the vertically oriented fluidic separation chamber through the fluidic separation detector, and
converting the growth rate $Q_C$ of the gaseous phase column to a production fluid gas flow rate $Q_G$.

22. The method as claimed in claim 21 wherein the fluidic supply and analysis unit converts the growth rate $Q_C$ of the gaseous phase column to the production fluid gas flow rate $Q_G$ by accounting for a gravitational separation rate $Q_S$ of the gaseous phase column resulting from gravitational forces in the vertically oriented fluidic separation chamber.

23. The method as claimed in claim 21 wherein converting the growth rate of the gaseous phase column to the production fluid gas flow rate $Q_G$ further comprises:
measuring a change of height $\Delta h$ of the gaseous phase column over a time $\Delta t$;
calculating an increase in gaseous volume $\Delta V$ as a function of $\Delta h$ and a cross sectional area of the vertically oriented fluidic separation chamber; and
calculating the production fluid gas flow rate $Q_G$ as a function of the $\Delta V$ and a gravitational separation rate $Q_S$, which accounts for volumetric growth of the gaseous phase column resulting from gravitational forces in the vertically oriented fluidic separation chamber.

24. The method as claimed in claim 23 wherein the method further comprises supplying a sufficient volume of the multiphase production fluid via the production fluid supply valve to ensure that a completely separated gaseous phase column resides within the vertically oriented fluidic separation chamber over the time $\Delta t$.

25. The method as claimed in claim 23 wherein the method further comprises supplying the sufficient volumes of the multiphase production fluid and a baseline liquid comprising water to the vertically oriented fluidic separation chamber via the production fluid supply valve and a baseline liquid supply valve to ensure that a completely separated gaseous phase column resides within the vertically oriented fluidic separation chamber over the time $\Delta t$.

26. The method as claimed in claim 21, further comprising:
maintaining laminar multiphase production fluid flow in the fluidic piping by maintaining a pressure drop across the multiphase production fluid flow in the fluidic piping and the vertically oriented fluidic separation chamber, as measured by the separation chamber pressure sensor, at less than about 1000 kPa; and
maintaining an average flow velocity of the multiphase fluid in the fluid analysis system at less than about 0.5 m/s.

27. The method as claimed in claim 21 further comprising stabilizing the the gas pressure within the vertically oriented fluidic separation chamber by controlling the inert gas exhaust valve, controlling a rate at which multiphase production fluid is supplied via the production fluid supply valve, or both.

28. The method as claimed in claim 27 wherein stabilizing the gas pressure further comprises controlling a rate at which a baseline liquid comprising water is supplied to the fluidic piping via a baseline liquid supply valve.

* * * * *